(12) United States Patent
Niznick et al.

(10) Patent No.: US 9,697,748 B1
(45) Date of Patent: Jul. 4, 2017

(54) TWO-PIECE FIXTURE MOUNT ASSEMBLY

(76) Inventors: Gerald A. Niznick, Las Vegas, NV (US); Ines M. Aravena, Camarillo, CA (US)

( * ) Notice: Subject to any disclaimer, the term of this patent is extended or adjusted under 35 U.S.C. 154(b) by 0 days.

(21) Appl. No.: 13/355,819

(22) Filed: Jan. 23, 2012

(51) Int. Cl.
*A61C 8/00* (2006.01)
*G09B 23/28* (2006.01)

(52) U.S. Cl.
CPC .............. *G09B 23/28* (2013.01); *A61C 8/005* (2013.01); *A61C 8/0018* (2013.01); *A61C 8/0066* (2013.01); *A61C 8/0022* (2013.01)

(58) Field of Classification Search
CPC ..... G09B 23/28; A61C 1/084; A61C 13/2656; A61C 2202/00; A61C 8/005; A61C 8/0066; A61C 8/0018; A61C 8/0022; A61C 8/0039; A61C 8/0069; A61C 8/0089; A61C 8/0057; A61C 8/0054; A61C 8/0065; A61C 8/0059
USPC ....................................... 433/172–175, 201.1
See application file for complete search history.

(56) References Cited

U.S. PATENT DOCUMENTS

| | | | |
|---|---|---|---|
| 6,561,805 B2 * | 5/2003 | Kumar ................... | A61C 8/008 206/368 |
| 7,338,286 B2 * | 3/2008 | Porter et al. .................. | 433/173 |
| 7,887,325 B2 * | 2/2011 | Whipple ....................... | 433/163 |
| 2009/0253098 A1 * | 10/2009 | Whipple ....................... | 433/174 |

* cited by examiner

*Primary Examiner* — Cris L Rodriguez
*Assistant Examiner* — Mirayda A Aponte
(74) *Attorney, Agent, or Firm* — Patrick Bright (57) ABSTRACT

A dental implant two-piece fixture mount has an implant fixture-mount base portion at its distal end and a snap-on, separate, separable top piece at its proximal end.

4 Claims, 10 Drawing Sheets

TWO-PIECE FIXTURE MOUNT ASSEMBLY

SUMMARY OF THE INVENTION

It is an object of this invention to provide a new and improved dental implant fixture mount for use in making highly accurate direct impressions.

This dental implant two-piece fixture mount may include an implant fixture-mount base portion at its distal end and a snap-on, separate, separable top piece at its proximal end. The top piece may include an internal through passage and a proximal insertion-tool-engaging surface such as a multi-sided, e.g. a four-sided/square, shape end. This proximal end may also include a plurality of integrally-formed, longitudinally-extending springy fingers. The top piece may include: (1) a distal, cylindrical skirt portion that comprises a plurality of distally-extending, flexible fingers, at least some fingers including protrusions on their distal, inner surface, or (2) a plurality of distal, flexible fingers at least one of which may include distal protrusions, and are of size and shape to engage a groove in an internal passage inside the fixture-mount base portion.

With this top piece having a distal skirt portion seated atop the fixture-mount base portion, the protrusions on the skirt's inner surface may snap into the groove on the fixture-mount base portion. With this top piece having a plurality of dental, flexible fingers, the protrusions on the distal, inner surfaces of the distal, flexible fingers may snap into an internal groove inside the internal passage of the fixture-mount base portion.

The top piece may also include an integrally-formed hex-shaped male member at its distal end, and a plurality of external flat surfaces, or both.

The fixture-mount base portion also has a separable, proximal portion that includes a groove, located on the external surface of, and near the bottom of this fixture-mount base portion. The fixture-mount base portion also has an internal, longitudinal through passage with a multi-sided surface, e.g., a hex-shaped surface, at a separable proximal portion or near the proximal opening into this passage to receive and engage with the male member at the distal end of the top piece. The fixture-mount base portion may have a plurality of flat, longitudinally extending surfaces that can be aligned with corresponding external flat surfaces on the top piece to assure accurate registration/alignment of the top piece and the fixture-mount base portion, and accurate, precise formation of direct impressions with the top piece. A hex-shaped or other wrench-engaging surface may lie within the internal passage, preferably in the top. The fixture-mount base portion's longitudinal passage is of size and shape to receive a fixation screw for attachment of the fixture-mount base portion to a dental implant.

Advantageously, the insertion-tool-engaging proximal end of the top piece, with or without the springy, integrally-formed fingers and/or multi-sided surface, may lie in the separable, proximal portion and can be used to carry a dental implant attached to the fixture mount to an insertion site in a patient's jawbone. After implant insertion, the top portion may be enveloped in impression material, and then detached from the fixture-mount base portion with the impression material. The fixture-mount base portion may then be unscrewed from the implant, inserted into the top portion enveloped in the impression material, and attached to an implant analog. The metal flats on the top portion and the corresponding metal flats on the fixture-mount base portion may be aligned to assure accuracy in forming a direct impression. After the replica stone model is created, the separable, proximal portion of the fixture-mount base portion is grinded down so a prosthesis can be inserted, and thereafter, attachment to the implant.

BRIEF DESCRIPTION OF THE DRAWINGS

This invention may be better understood from the following description of some exemplary embodiments of the invention, taken in conjunction with the accompanying drawings in which like reference numerals refer to like parts and in which.

DETAILED DESCRIPTION OF THE DRAWINGS

FIGS. 1 to 6 show fixture mount assembly 12 connected to endosseous dental implant 11 by fixation screw 31. Screw 31 fits inside longitudinal through passage 34 in the fixture-mount base portion 15 of fixture mount 12. Head 31a of screw 31 engages shoulder 46 formed inside passage 34 as threads 30 on the shank portion 47 of screw 31 engage threads 32 inside internal passage 33 in implant 11.

Fixture-mount base portion 15 of fixture mount 12 includes flat top surface 48, separable, frusto-conical shaped, proximal portion 25, external, circumferential groove/notch 26, frusto-conical side wall 13, side wall flat 16, distal inwardly-projecting surface 27, distal cylindrical surface 28, and distal, multi-sided, projection 29, here including a plurality of flat, contiguous surfaces.

Top piece 14 of fixture mount 12 includes flat top surface 49, with a chamfered opening into internal passage 34, multi-sided, wrench-engaging top portion 21, here including four flat sides, a plurality of integrally-formed springy fingers 20, cylindrical external side wall portion 22, external, outwardly-tapering side wall portion 17, distal to portion 22, flexible skirt portion 18, and distal, multi-sided projection 23. Projection 23 includes a plurality, here six, of contiguous flat sides. Projection seats anti-rotationally into internal, multi-sided region 50 inside passage 34. On the inner, distal surfaces of skirt 18 are projections 51 and 52 that engage, and seat in, notch/groove 26 when top piece 14 is seated on fixture-mount base portion 15. External flat surface 16 on the side wall of fixture-mount base part 15 may be aligned with external flat surface on top piece 14, or may be aligned to multi-sided projection 23, to assure proper placement and alignment of a prosthesis attached to fixture-mount base portion 15. These flat surfaces are preferably placed parallel to, and facing the buccal or lingual sides of the jawbone placement site for the implant attached to the fixture mount.

Implant 11 includes external micro-grooves 36, eternal threads 37 of a first desired pitch, and external threads 38 of a second, larger pitch than threads 37. Implant 11 also includes self-tapping external surface 39 at its distal end.

Figure 1:
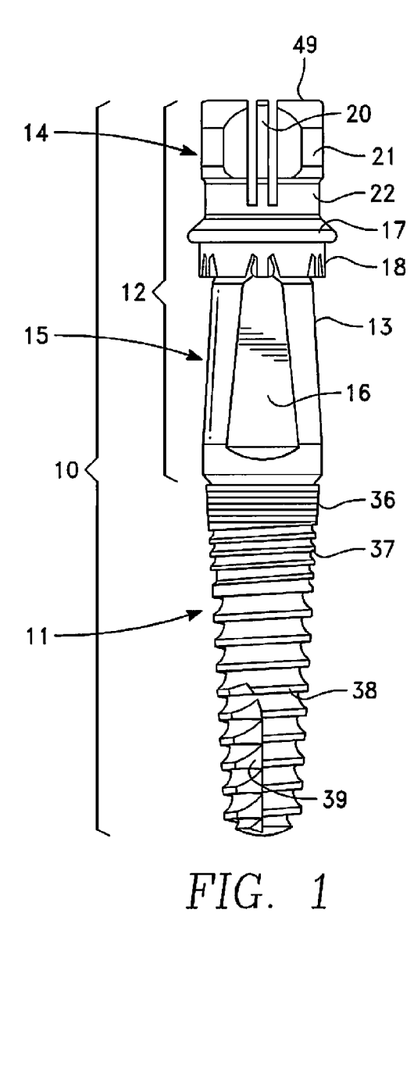
FIG. 1 shows an embodiment of a fixture mount assembled on a dental implant.
Figure 2:
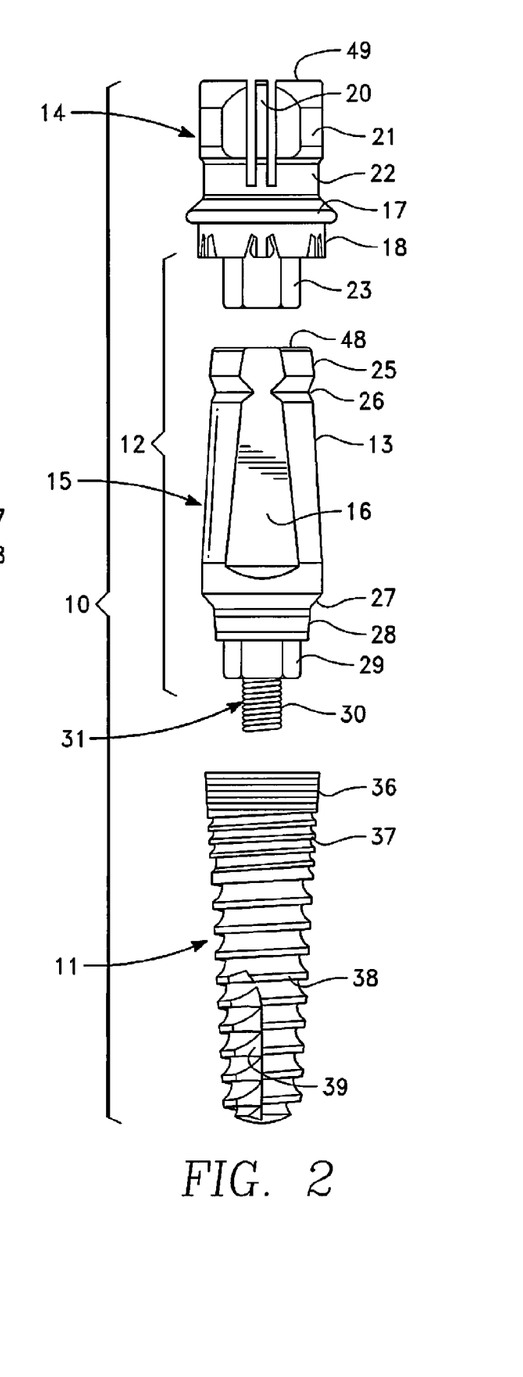
FIG. 2 shows the two-part fixture mount of FIG. 1 separated into its two parts and separated form the implant shown in FIG. 1.
Figure 3:
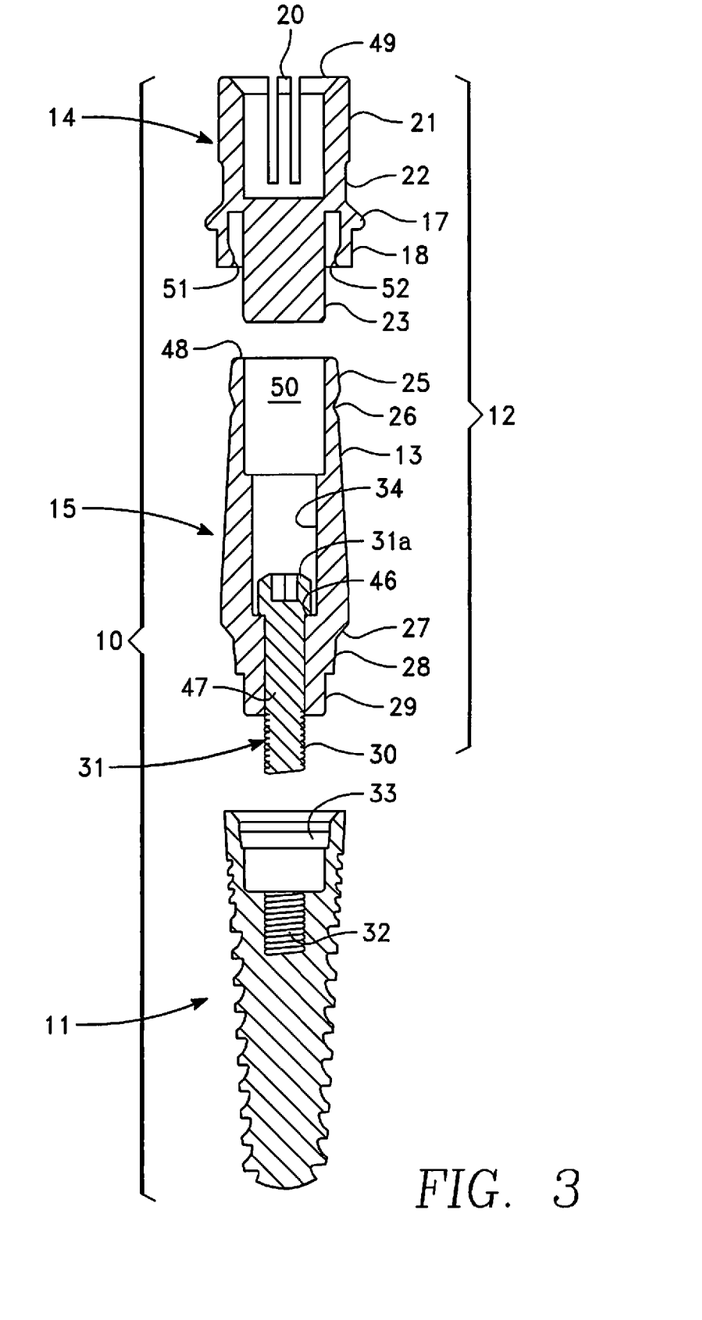
FIG. 3 shows a vertical cross section of the two-part fixture mount and implant of FIGS. 1 and 2, here including a fixation screw that attaches the fixture mount to the implant.
Figure 4:
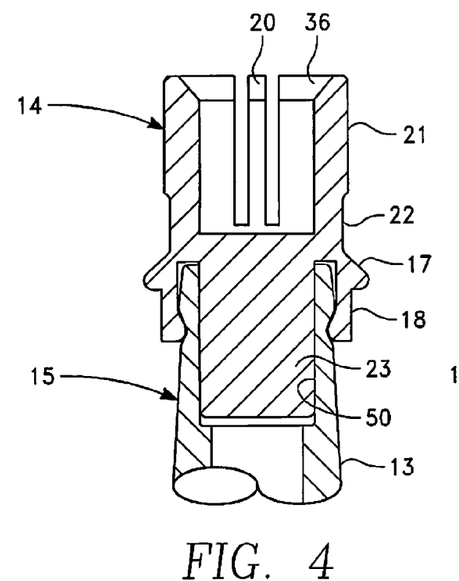
FIGS. 4 and 5 show enlarged elevation views, in vertical cross-section, of the two parts of the fixture mount of FIGS. 1 to 3 connected to one another, and separated from one another, respectively.
Figure 5:
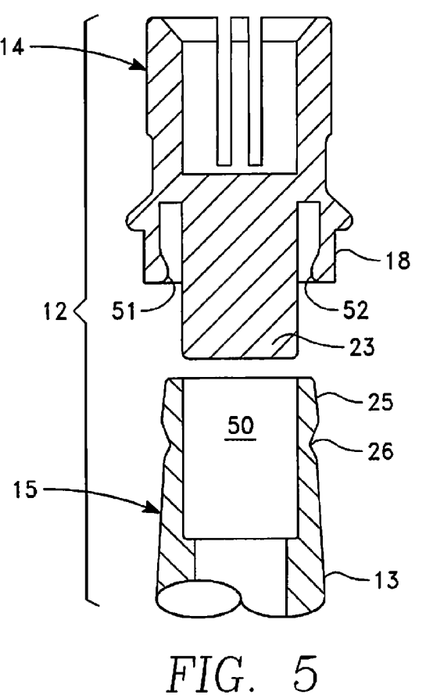
Figure 6:
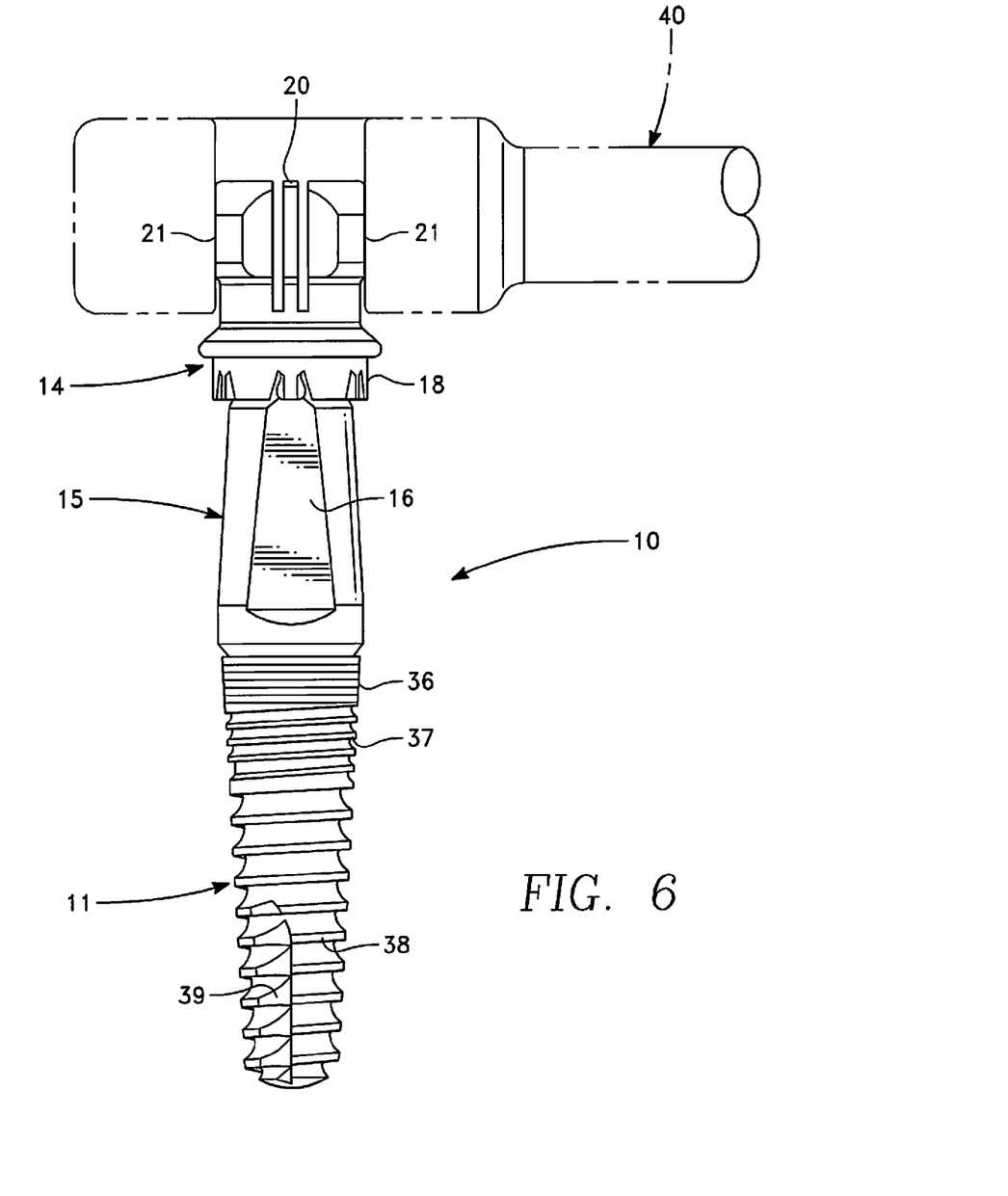
FIG. 6 shows a ratchet attached to the top piece of the fixture mount shown in FIGS. 1 to 5.
Figure 7:
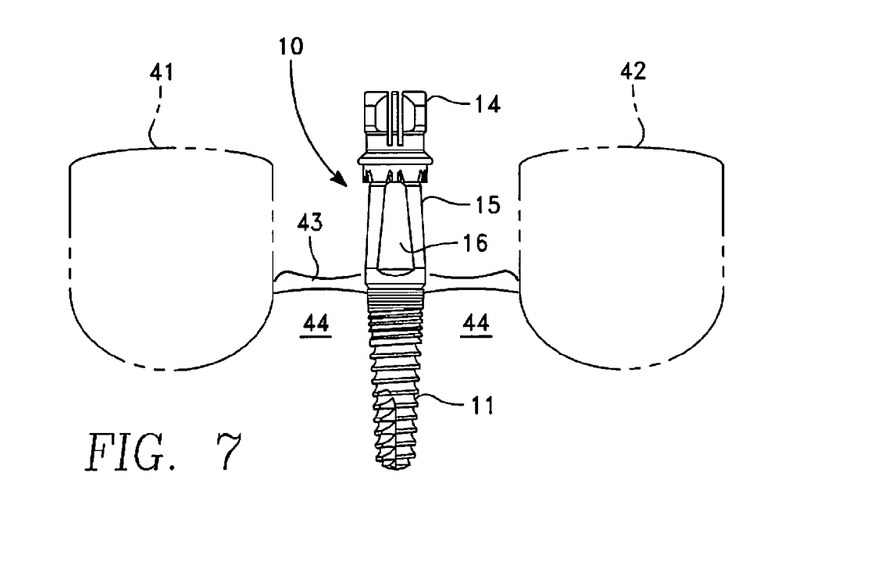
FIG. 7 shows the fixture mount of FIGS. 1 to 6, with the entire assembly placed in an opening in the jawbone of a patient.

FIG. 6 shows ratchet 40 attached to the top of assembly 10 to screw implant 11, and attached fixture mount 12, into an opening in the jawbone of a patient.

Figure 8:
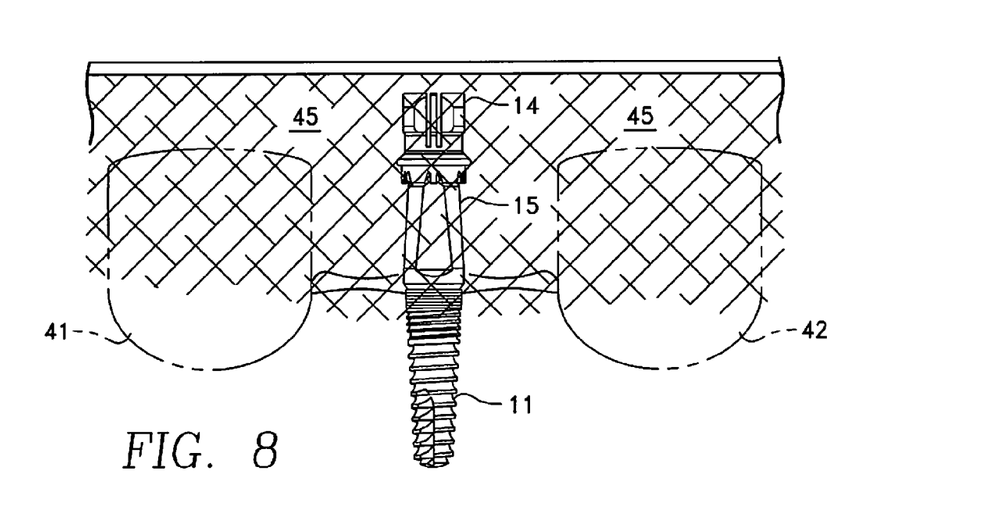
FIG. 8 shows the assembly of FIG. 7 placed into impression material.
Figure 9:
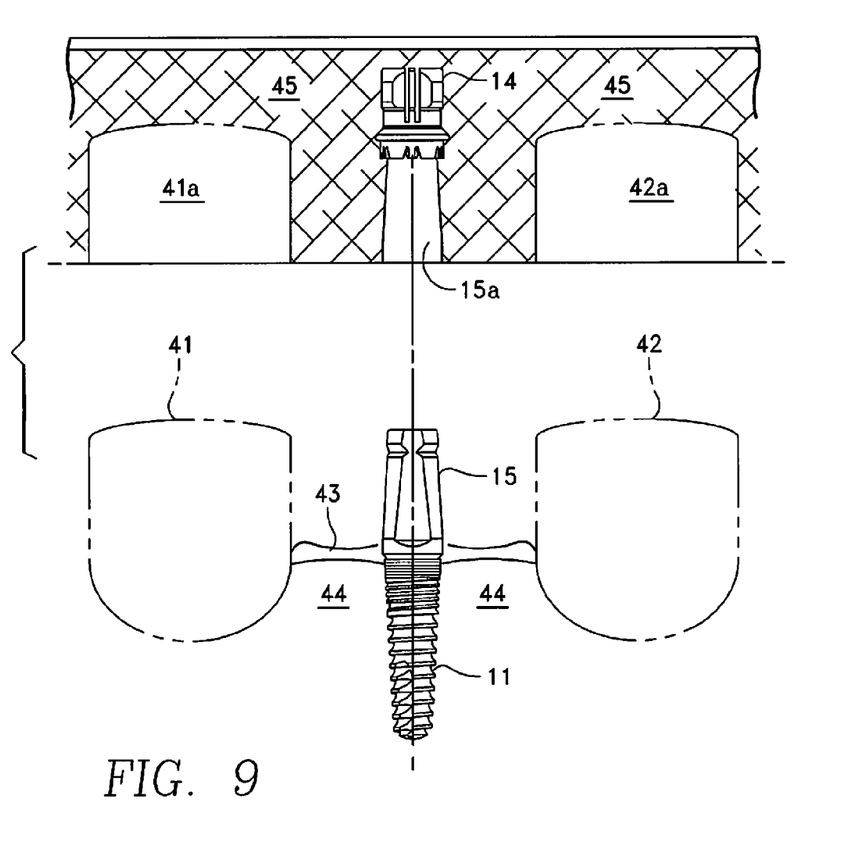
FIG. 9 shows the separation of the top piece of the fixture mount shown in FIG. 8, embedded in impression material, and separated from the fixture-mount base portion of the fixture mount.
Figure 10:
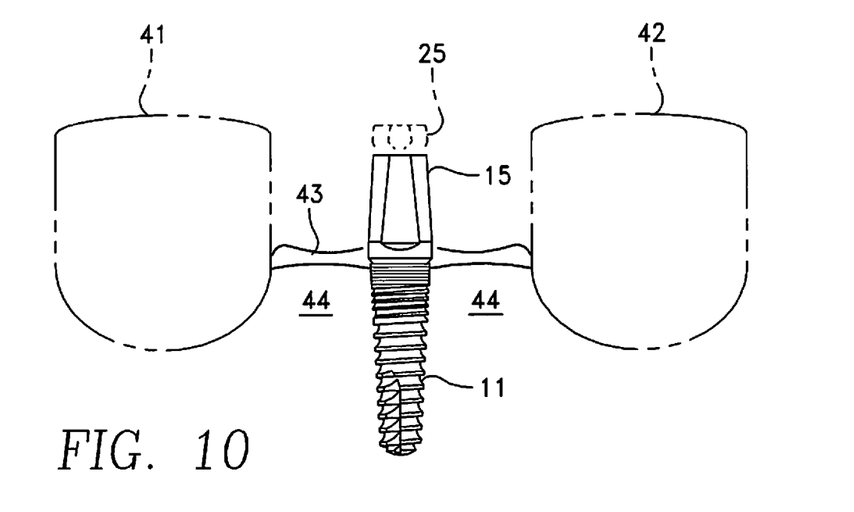
FIG. 10 shows the formation of an abutment by separation of the proximal end of the fixture-mount base portion of the fixture mount.
Figure 11:
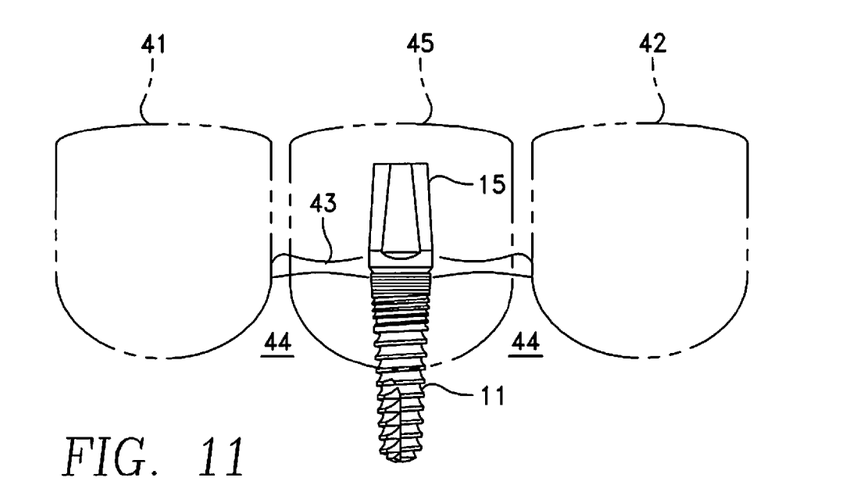
FIG. 11 shows a prosthesis attached to the abutment formed in FIG. 10.
Figure 12:
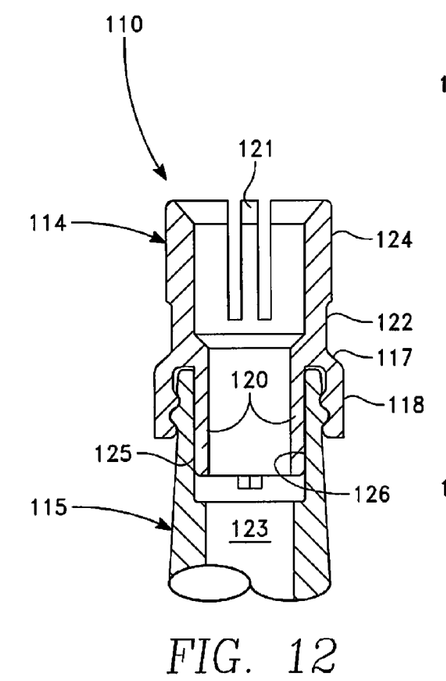
FIGS. 12 and 13 show an alternative to the fixture mount embodiment of FIGS. 1 through 11, with the distal skirt on the top piece here including, on its distal inner surface, a groove or notch for engaging a circumferential protrusion on the external wall surface of the fixture-mount base part.
Figure 13:
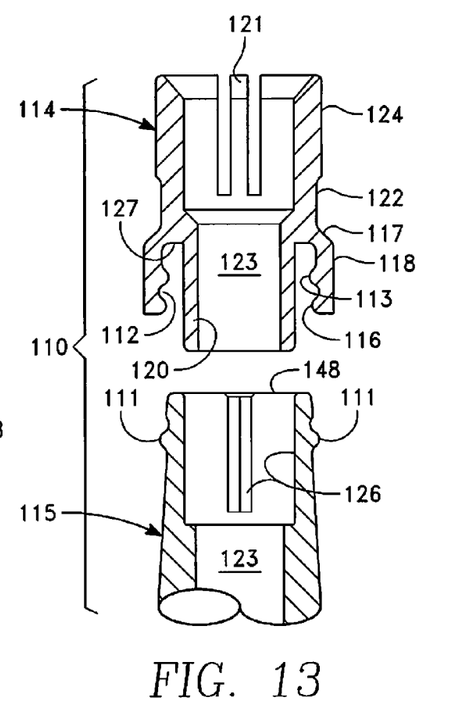

FIGS. 7 to 11 show the placement of assembly 10 in an opening in the soft tissue 43 and the jaw bone 44 of a patient, here between adjacent teeth 41 and 42. FIG. 8 shows the placement of impression material 45 over assembly 12. FIG. 9 shows separation of top piece 14, embedded in impression material 45, from fixture-mount base portion 15 and implant 11. FIG. 10 shows separation of separable portion 25 from fixture-mount base portion 15 to form an abutment that receives a prosthesis 45, as shown in FIG. 11.

FIGS. 12, 13, 16 and 17 show a second fixture mount embodiment 110, which includes top piece 114 and fixture-mount base portion 115. Top piece 114 includes an insertion-tool engaging, multi-sided proximal portion 124 with springy fingers 121 for firm engagement with an insertion tool such as a ratchet. Distal to portion 124 are unthreaded, narrower diameter surface 122, outwardly-extending surface 117, and skirt portion 118. Also extending distally from portion 124 is portion 120 with its external, multi-sided external surfaces 125 that engage complementary multi-sided surfaces 126 inside through passage 123 inside fixture-mount base part 115, on the inner, distal surfaces of skirt 118 1s groove/notch 112 formed by circumferential, parallel protrusions 113 and 116. Groove/notch 112 fits over external protrusion 111 on the external sidewall surface of fixture-mount base portion 115, holding top piece 114 in place atop fixture-mount base portion 115. Surface 127 sits on surface 148 when top piece 114 is in place atop fixture-mount base portion 115.

Figure 16:
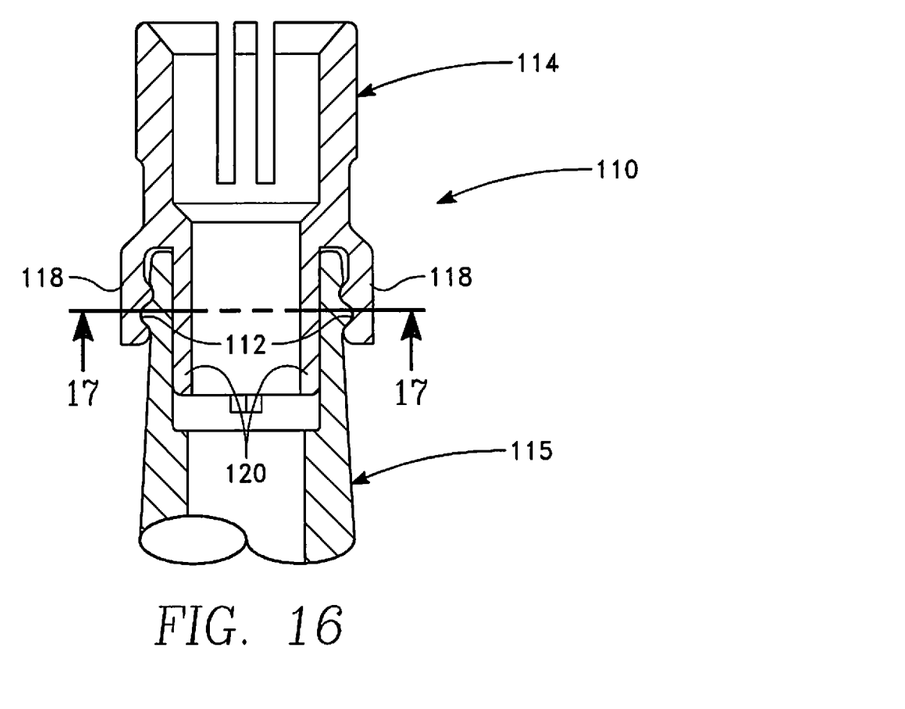
FIGS. 16 and 17 show how alignable flat external and or internal surfaces on the top piece and on the fixture-mount base part, in the fixture mount embodiment of FIGS. 12 and 13, assure proper re-alignment of the top piece and fixture-mount base part after separation of these two parts from one another.
Figure 17:
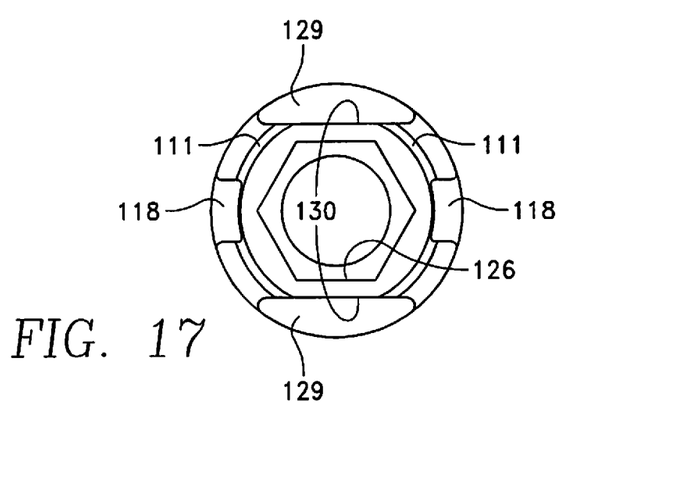

FIGS. 16 and 17 show that flat external sidewall surfaces on inner surfaces of top piece 114 align with corresponding flat external surfaces 129 and 130 on fixture-mount base portion 115 to provide correct, accurate alignment of the top piece and the fixture-mount base portion to one another. The top piece 114 has external surfaces 126 that align with the external surfaces and or corresponding wrench-engaging surface of the fixture-mount base portion 115.

Figure 14:
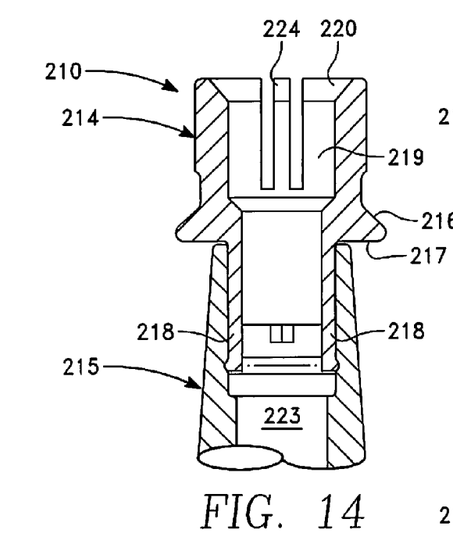
FIGS. 14, 14A and 15 show another alternative to the embodiment of FIGS. 1 through 11 and FIGS. 12 and 13, here with a top piece that fits inside of, and engages, an internal passage in the fixture-mount base part.
Figure 14A:
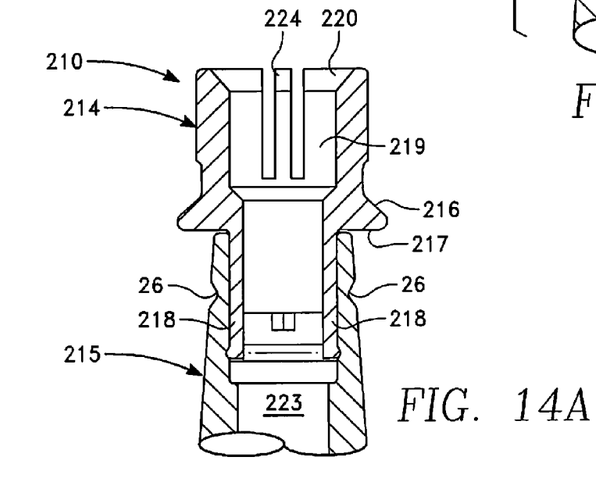
Figure 15:
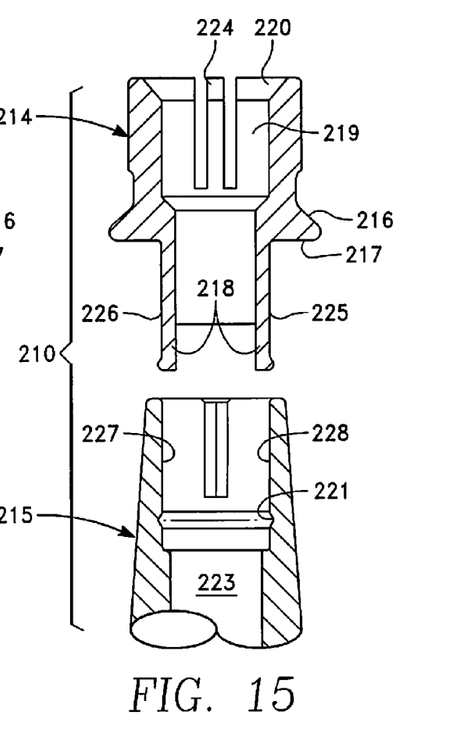

FIGS. 14, 14A and 15 show another fixture mount embodiment 210 with top piece 214 and abutment portion 215. Top portion 214 includes insertion tool-engaging portion 214 and springy fingers 224 to provide firm engagement with such tools. Distal to top portion 214 are outwardly extending sloping flange 216 with flat under surface 217. Extending distally from surface 217 is extension portion 218 that fits inside of internal passage 223 in fixture-mount base portion 215, and engages internal sidewall groove/notch 221 in passage 223 to hold top piece 214 in place atop fixture-mount base portion 215. Portion 218 is hex-shaped, such that flat surfaces 225 and 226 engage corresponding flat surfaces 228 and 227 in internal passage 223. Top piece 214 has an internal through passage 219 with lead in bevel 220 at its proximal opening. FIG. 14A is an alternative to the embodiment of FIG. 14, and includes circumferential grove 26 on the external wall surface of abutment portion 215. Groove 28 may engage complementary structure, such as projection 113 (see FIG. 13) on the internal wall surface of skirt 118. Groove 26 may also/alternatively be a weakened area for severing the proximal portion from abutment portion 115.

Although some preferred embodiments of the invention have been described above by way of example only, it will be understood by those skilled in the field that modifications may be made to the disclosed embodiments without departing from the scope of the invention, which is defined by the appended claims.

We claim:

1. A two-piece dental implant fixture mount includes a first piece comprising an implant fixture-mount base portion at the distal end of said fixture mount, and a second piece comprising a snap-on, separable top piece at the proximal end of said fixture mount, said second piece including a proximal insertion-tool-engaging portion, a distal insertion projection, and a distal skirt with protrusions on the distal surface of said skirt, said first piece including a separable, integrally-formed, proximal portion that includes a separation groove near the bottom of the external surface of said separable, integrally-formed, proximal portion, and a longitudinal through passage, and, inside said first piece, an internal groove for engaging said protrusions upon insertion of said second piece into said first piece said through passage having a size and shape to receive a fixation screw for attachment of said first piece to a dental implant, and having an internal, multi-sided region of a size and shape to anti-rotationally engage said distal insertion projection.

2. The fixture mount of claim 1, wherein said first and second pieces include at least two alignable flat external and/or internal surface regions, and a distal, multi-sided protrusion for engagement with a complementary, multi-sided inner surface in a passage inside a dental implant.

3. A two-piece dental implant fixture mount includes two separate pieces: a first piece comprising an implant fixture-mount base portion at the distal end of said fixture mount, and a second piece comprising a snap-on, separate, separable top piece at the proximal end of said fixture mount, said second piece including an insertion-tool-engaging portion, a distal insertion projection, and a distal cylindrical skirt with a plurality of protrusions on the skirt's surface, said first piece including a separable, integrally-formed, proximal portion, and a longitudinal through passage that is of a size and shape to receive a fixation screw for attachment of said first piece to a dental implant, and that includes an internal, multi-sided region of a size and shape to anti-rotationally engage said distal insertion projection.

4. A two-piece dental implant fixture mount includes two separate pieces: a first piece comprising an implant fixture-mount base portion at the distal end of said fixture mount, and a second, separate piece comprising a snap-on, separable top piece at the proximal end of said fixture mount, said second piece including an insertion-tool-engaging portion, a distal insertion projection, and a distal cylindrical skirt with a plurality of protrusions on the skirt's surface, said first piece including a separable, integrally-formed proximal portion, and a longitudinal through passage that is of a size and shape to receive a fixation screw for attachment of the first piece to a dental implant, and that includes an internal, multi-sided region of a size and shape to anti-rotationally engage said distal insertion projection.

\* \* \* \* \*